(12) United States Patent
Pusineri et al.

(10) Patent No.: US 6,559,199 B1
(45) Date of Patent: May 6, 2003

(54) SILICONE ELASTOMER SYSTEM HAVING BIOCIDE PROPERTIES USEFUL IN PARTICULAR FOR MAKING IMPRESSIONS IN DENTISTRY

(75) Inventors: Christian Pusineri, Serezin du Rhone (FR); Marco Del Torto, Solbiate Olona (IT)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/744,882

(22) PCT Filed: Jul. 30, 1999

(86) PCT No.: PCT/FR99/01885

§ 371 (c)(1), (2), (4) Date: Apr. 30, 2001

(87) PCT Pub. No.: WO00/07546

PCT Pub. Date: Feb. 17, 2000

(30) Foreign Application Priority Data

Jul. 31, 1998 (FR) .............................. 98 10023

(51) Int. Cl.$^7$ ................................ A61K 6/10
(52) U.S. Cl. ...................... 523/109; 528/14; 528/15; 528/31; 528/32; 528/38; 528/12; 524/159; 524/588; 264/16; 433/214; 424/53; 525/478; 525/474
(58) Field of Search .............................. 528/14, 15, 31, 528/32, 34, 12; 524/588, 159; 523/109; 264/16; 433/214; 525/474, 478

(56) References Cited

U.S. PATENT DOCUMENTS 4,500,339 A * 2/1985 Young et al.
5,874,164 A * 2/1999 Caldwell

FOREIGN PATENT DOCUMENTS

| EP | 0 265 776 | 5/1988 |
| EP | 0 361 301 | 4/1990 |
| EP | 0 493 186 | 7/1992 |
| FR | 2 707 660 | 1/1995 |
| FR | 2 750 598 | 1/1998 |

* cited by examiner

Primary Examiner—Robert Dawson
Assistant Examiner—Kuo-Liang Peng
(74) Attorney, Agent, or Firm—Burns, Doane, Swecker & Mathis, L.L.P.

(57) ABSTRACT

An elastomer system having biocide properties is described, useful, in particular, for dental impressions. An efficient system is provided for destroying microbes, without adversely affecting the crosslinking properties and the mechanical qualities of RTV 2 elastomers. Said system comprises an RTV 2 silicone, preferably SiH/SiVi polyaddition product and a biocide selected among active chlorine precursors, preferably among N-chloramines. The system may include functional additives (silicon fillers, alumina, paraffin, vaseline oil). As for the biocide, it can be provided with an antiseptic auxiliary adjuvant along with EDTA-type sequestering agents.

16 Claims, No Drawings

SILICONE ELASTOMER SYSTEM HAVING BIOCIDE PROPERTIES USEFUL IN PARTICULAR FOR MAKING IMPRESSIONS IN DENTISTRY

The field of the present invention is that of organosilicon systems comprising a polyorganosiloxane composition which can be hardened into an elastomer and at least one biocidal active ingredient chosen from chlorine derivatives. The applications targeted by such systems are in particular the taking of impressions and, still more particularly, the taking of dental impressions in the context of the production of prostheses.

The present invention therefore relates to a silicone elastomer system having biocidal properties and which can be used in particular for the taking of impressions, for example dental impressions.

The subject of the invention is also a material for taking impressions, in particular dental impressions, comprising the abovementioned silicone elastomer system.

Finally, the invention is aimed at the use of the system or of the material for the taking of impressions, for example dental impressions, as well as a process for preparing the said system and/or the said material.

The notion of biocidal activity relates to the fields of hygiene, comfort and medical and paramedical applications. The use of silicone elastomers is very widespread in these fields. This is partly due to the fact that silicone elastomers offer, on the one hand, a wide diversity of chemical, mechanical and physical characteristics, and, on the other hand, a nontoxic, nonirritant and nonallergenic character. In addition, silicone elastomers constitute poor culture substrates for microorganisms, which confers on them remarkable properties with regard to hygiene.

It is moreover known that silicones of the cold-vulcanizable elastomer type which advantageously exist in the form of two components (EVF 2 or RTV 2) are particularly suitable for the art which consists in taking impressions, in reproducing and in creating forms. This is explained by the fact that these silicones are endowed with properties of fluidity and film-forming ability before crosslinking, which makes possible the taking of an impression of any model or of any form. The subsequent crosslinking which causes the hardening of the silicone elastomer makes it possible to constitute suitable moulds from the impressions. The good thermal stability of the crosslinked EVFs (or RTVs) allows the moulds made from these materials to withstand the high melting points of certain moulding materials such as metals.

The production of moulds from EVF or RTV silicone elastomer is particularly advantageous in order to obtain small series for which the cost and the period of production of the mould are not excessive, unlike what is observed when the mould is metallic.

There is a link between this "moulding" application of EVFs or RTVs and their use in the health field since dentists, chiropodists and plastic surgeons use silicone elastomers to produce moulds for dentures or for corrective forms (inserts, breast prostheses).

Thus, without limitation, EVFs or RTVs are particularly advantageous in the field of the taking of impressions, in particular dental impressions, because they are available in the non-crosslinked state under fluid- or paste-type rheologies. Moreover, they crosslink within a few minutes at room temperature; they are nontoxic and satisfy European regulations in the pharmaceutical field. However, the taking of impressions remains subject to surface or even intermass contaminations by pathogenic microorganisms and thus becomes vectors for propagation and dissemination of microbes between the dental practice and the prosthetist's laboratory.

To attempt to counteract this, it is possible to conventionally carry out a disinfection treatment of the impression material by bringing it into contact with a conventional antiseptic, for example by immersion or by spraying. This type of disinfection treatment limited to the surface is of course not completely without efficacy in the desired attempt to break the contamination chain, but it remains totally inadequate. In addition, this additional step of surface disinfection represents a constraint which practitioners can gladly do without.

In the context of a search for efficacy in the area of decontamination of these materials for taking dental impressions in particular, the solution consisting in incorporating into the material itself an antiseptic which will perform its primary function both intermass and at the surface, is also known. By way of illustration of this technical proposition, there may be mentioned European patent application EP No. 0 361 301 which describes the introduction of a biocide into an alginate-based material for taking dental impressions. Alginates are a hardly convincing alternative to the EVFs or RTVs. The biocidal agent involved exists in the form of an aqueous solution of quaternary ammonium salts and of compounds based on guanidine and its derivatives. This solution replaces the water necessary for the preparation of the alginate paste.

There is also known outside the specific application "taking of dental impressions" but still in the context of the biocidal silicone elastomers used in the hygiene and health field, European patent application EP-A-0 493 186 which describes a biocidal organosilicon system comprising:
- a two-component organopolysiloxane composition which can be crosslinked at room temperature or in the presence of heat, by in particular polyaddition reactions,
- as well as a biocidal system consisting of a salt of a hydracid or of an inorganic oxacid or of an organic acid derived from a linear polymeric biguanide: poly(hexamethylene-biguanide). This silicone elastomer with biocidal activity is intended to be incorporated into sponges so as to combat bacterial proliferation both during the period of storage and during the period of use of the said sponges.

There should also be mentioned in this review of the prior art French patent application 93 08 114 published under No. 2 707 660 and which relates to a silicone elastomer system obtained by crosslinking a composition comprising:
- A—100 parts by weight of α,ω-di(hydroxy) diorganopolysiloxane silicone;
- B—from 2 to 20 parts by weight of a crosslinking silane containing a hydrolysable group;
- C—from 0 to 150 parts by weight of an inorganic or organic filler;
- D—1 to 150 parts by weight per 100 parts of A+B+C, of a solid inorganic or organic compound capable of releasing active chlorine in contact with water or moisture (preferably calcium hypochlorite);
- E—optionally a polycondensation crosslinking catalyst.

This composition contains at least 0.01% of its weight of water provided and optionally generated intrinsically and optionally provided extrinsically. In this patent application, the use of such a system as agent for releasing active chlorine, in particular for the treatment of water, is recommended.

The elastomer silicone system according to this patent application is strictly limited to the silicone of the α,ω-di (hydroxy)diorganopolysiloxane type which is crosslinkable by polycondensation. In addition, the silicone elastomer system disclosed in this patent application is described as being capable of being used for the production of seals or of films useful in the fields of hygiene and of sanitary applications. Another application envisaged in this prior art reference is that of the treatment of water. The system is in this case provided in the form of silicone matrix contained in a cartridge which gradually releases the calcium hypochlorite biocidal active ingredient. The application of the system as material for the taking of impressions, in particular dental impressions, is not at all dealt with in this patent application.

It was found that the antiseptics used within the mass of materials as described in EP-A-0 361 301, in EP-A-0 493 186 and in FR-A-2 707 660 do not meet the specifications specific to the applications of elastomer materials in the field of hygiene and health and, more particularly but without limitation, in the case of materials for taking impressions, in particular dental impressions.

The specifications considered comprise, inter alia, the following specifications:

the material loaded with blocide should be compatible for contact with the skin and the mucous membranes, in particular the buccal mucous membranes: it should be nontoxic, nonallergenic and nonirritant at the applicable doses;

the material should contain a sufficient content of biocide in order to be able to develop at the surface the desired antiseptic activity regardless of the mechanism of action: contact activity and/or release of small quantities of active product;

the biocidal agent should not develop any inhibitory activity towards the crosslinking catalysts, in particular towards platinum catalysts in the case of the polyaddition EVF or RTV system;

the presence of biocidal agent in the material should not interfere with and hamper the technical performance features of the elastomer material; in particular, "the crosslinkability", the setting time, the rheological properties before crosslinking, the mechanical properties after crosslinking, the dimensional stability and the thermal stability, should not be affected.

In such a technical context, one of the essential objectives of the present invention is to provide a silicone elastomer system with biocidal properties and which can be used in particular for the taking of impressions, for example dental impressions, it being necessary for the said system, as far as possible, to comply with the abovementioned specifications.

Another essential objective of the invention is to provide a biocidal silicone elastomer system, in particular of the EVF 2 or RTV 2 type, which is simple to obtain, is inexpensive, is effective from the point of view of the antiseptic activity and which possesses excellent physical and chemical properties during use.

Another essential objective of the invention is to provide a material for the taking of dental impressions in particular which satisfies the specifications aimed at above for the system.

Another essential objective of the invention is to propose the use of a biocidal silicone elastomer system for the taking of impressions, in particular dental impressions.

Another essential objective of the present invention is to provide a process for preparing the abovementioned system which is industrial and not very costly.

To achieve these objectives, among others, the inventors have had the merit of bringing up-to-date quite surprisingly and unexpectedly and after long and laborious research studies and experiments, a judiciously selected class of biocidal agents which are active chlorine promoters.

Hence it follows that the present invention relates to a silicone elastomer system, which can be used in particular for taking impressions, in particular dental impressions, having biocidal properties and characterized in that it essentially comprises:

(I) at least one polyorganosiloxane (POS) composition which can be crosslinked or which is crosslinked in elastomer form, and which optionally comprises at least one crosslinking catalyst, (II) and at least one biocidal agent chosen from active chlorine precursors, preferably from N-chlorinated compounds and more preferably still from N-chloramines;

excluding silicone-based materials, in particular for dental impressions, comprising a hydrophobic antiseptic agent incorporated into the mass of the silicone and capable of being gradually released as far as the surface of the impression material, this antiseptic agent consisting in particular of ethylenediaminetetraacetic acid, benzalkonium chloride and sodium tosylchloramide or one of its analogues; and with the condition according to which in the case where the composition (I) comprises α,ω-di(hydroxy) POSs which can be crosslinked by polycondensation, then the concentration $C_{II}$ of biocidal agent, expressed in % by weight relative to the total mass (I+II), is:

$C_{II} < 1$ preferably $C_{II} \leq 0.8$ and more preferably still $0.001 \leq C_{II} \leq 0.5$.

Considered as "biocides" for the purposes of the invention are the agents endowed with destructive properties towards live microorganisms of any type: bacteria, viruses, fungi, yeasts, in vegetative form (spores) or otherwise.

In addition to the advantageous selection of the biocidal agent from active chlorine precursors, the invention is also based on the qualitative and quantitative choice of the compatible silicone elastomers. The synergistic combination of the POS composition I and of the biocidal agent II leads to a system or to a silicone elastomer material having the following advantages:

stably antiseptic over time, endowed with all the advantageous properties of non-crosslinked elastomers (fluidity, film-forming ability) and of crosslinked elastomers (hardness, dimensional stability, thermal stability);

low production cost, in particular for making industrial moulds.

According to one characteristic of the invention, the POS composition (I) comprises POSs which can be crosslinked by polyaddition and moreover the concentration $C_{II}$ of biocidal agent, expressed in % by weight relative to the total mass (I+II), is:

$C_{II} \leq 1$ preferably $C_{II} \leq 0.8$ and more preferably still $0.001 \leq C_{II} \leq 0.5$.

It is of particular interest to note that, at these low concentrations, the biocidal agent selected according to the invention is perfectly effective as regards the antiseptic activity, without as a result hampering the reactivity of the polyaddition EVFs or RTVs forming the silicone elastomer.

It is evident from the above that the POS composition (I) is preferably a polyaddition silicone composition which can be hardened to an elastomer by hydrosilylation reactions, characterized in that it comprises:

($I_a$)—at least one diorganopolysiloxane oil having, per molecule, at least two alkenyl, preferably vinyl, groups linked to the silicon;

($I_b$)—at least one diorganopolysiloxane oil having, per molecule, at least three hydrogen atoms linked to the silicon, ($I_c$)—a catalytically effective quantity of a catalyst which is in general a compound of a metal of the platinum group.

The quantities of ($I_a$) and ($I_b$) are generally chosen so that the molar ratio of the hydrogen atoms linked to the silicon in ($I_b$) to the vinyl radicals linked to the silicon in ($I_a$) is generally between 0.4 and 10, preferably between 0.6 and 5. This ratio however may be between 2 and 5 if it is desired to make elastomer foams.

The alkenyl groups in ($I_a$) and the hydrogen atoms in ($I_b$) are generally linked to different silicon atoms.

These compositions crosslink by addition reaction (also called hydrosilylation reaction), catalysed by a compound of a metal of a platinum group, of an alkenyl group of the organopolysiloxane ($I_a$) on a hydride function of the organopolysiloxane ($I_b$).

The alkenylated organopolysiloxane ($I_a$) may be an organopolysiloxane having siloxyl units of formula:

  (1)

in which Y is a vinyl group, Z is a monovalent hydrocarbon group which does not have an unfavourable action on the activity of the catalyst, Z is generally chosen from alkyl groups having from 1 to 8 carbon atoms inclusive such as methyl, ethyl, propyl and 3,3,3-trifluoropropy groups and aryl groups such as xylyl, tolyl and phenyl, a is 1 or 2, b is 0, 1 or 2 and a+b is between 1 and 3, optionally all the other units being units having the average formula:

  (2)

in which Z has the same meaning as above and c has a value between 0 and 3.

The organopolysiloxane $I_b$ may be an organohydrogenopolysiloxane comprising siloxyl units of formula:

  (3)

in which W is a monovalent hydrocarbon group having no unfavourable action on the activity of the catalyst and having the same definition as Z, d is 1 or 2, e is 0, 1 or 2, d+e has a value between 1 and 3, optionally all the other units being units having the average formula:

  (4)

in which W has the same meaning as above, g has a value between 0 and 3.

All the limiting values of a, b, c, d and g are included.

The organopolysiloxane ($I_a$) may consist solely of units of formula (1) and may contain, in addition, units of formula (2).

The organopolysiloxane (A) may have a linear branched cyclic or lattice structure. The degree of polymerization is 2 or more and is generally less than 5 000. Moreover, if the organopolysiloxane ($I_a$) is linear, it has a viscosity at 25° C. of less than 500 000 mPa·s.

Z Is generally chosen from methyl, ethyl and phenyl radicals, at least 60 mol % of the Z radicals being methyl radicals.

The organopolysiloxanes ($I_a$) and ($I_b$) are well known and are for example described in patents U.S. Pat. No. 3,220, 972, U.S. Pat. No. 3,284,406, U.S. Pat. No. 3,436,366, U.S. Pat. No. 3,697,473 and U.S. Pat. No. 4,340,709.

Examples of siloxyl units of formula (1) are the vinyldimethylsiloxyl unit, the vinylphenylmethylsiloxyl unit, the vinylsiloxyl unit and the vinylmethylsiloxyl unit.

Examples of siloxyl units of formula (2) are $SiO_{4/2}$ dimethylsiloxane, methylphenylsiloxane, diphenylsiloxane, methylsiloxane and phenylsiloxane units.

Examples of organopolysiloxane ($I_a$) are dimethylpolysiloxanes with dimethylvinylsiloxyl ends, methylvinyldimethylpolysiloxane copolymers with trimethylsiloxyl ends, methylvinyldimethylpolysiloxane copolymers with dimethylvinylsiloxyl ends, cyclic methylvinylpolysiloxanes.

The organopolysiloxane ($I_b$) may consist solely of units of formula (3) or may comprise in addition units of formula (4).

The organopolysiloxane ($I_b$) may have a linear or branched, cyclic or lattice structure. The degree of polymerization is 2 between and 5 000.

The group W has the same meaning as the group Z above.

Examples units of formula (3) are:

The examples of units of formula (4) are the same as those given above for the units of formula (2).

Examples of organopolysiloxane ($I_b$) are dimethylpolysiloxanes with hydrogenodimethylsilyl ends, dimethylhydrogenopolysiloxane copolymers with trimethylsiloxyl ends, dimethylhydrogenomethylpolysiloxane copolymers with hydrogenodimethylsiloxyl ends, hydrogenomethylpolysiloxanes with trimethylsiloxyl ends, cyclic methylvinylpolysiloxanes.

The organopolysiloxane ($I_a$) and/or the organopolysiloxane ($I_b$) may be diluted in a nontoxic organic solvent compatible with silicones.

The organopolysiloxanes ($I_a$) and ($I_b$) in the form of a lattice are commonly called silicone resins.

The bases of polyaddition silicone compositions may comprise only linear organopolysiloxanes (1) and (2) such as for example those described in the abovementioned American patents: U.S. Pat. No. 3,220,972, U.S. Pat. No. 3,697,473 and U.S. Pat. No. 4,340,709, or may comprise both branched and lattice organopolysiloxanes ($I_a$) and ($I_b$) such as for example those described in the abovementioned American patents: U.S. Pat. No. 3,284,406 and U.S. Pat. No. 3,436,366.

The polyaddition composition may comprise, in addition, from 5 to 40 parts by weight of polydimethylsiloxane oil(s) blocked at each of the chain ends by a $(CH_3)_3SiO_{0.5}$ unit, having a viscosity at 25° C. of between 10 and 5 000 mPa·s per 100 parts of organopolysiloxanes ($I_a$) and ($I_b$)

The catalysts ($I_c$) are also well known. The compounds of platinum and rhodium are preferably used. It is possible to use the complexes of platinum and of an organic product described in American patents U.S. Pat. No. 3,195,601, U.S. Pat. No. 3,159,602, U.S. Pat. No. 3,220,972 and European patents EP-A-57 459, EP-A-188 978 and EP-A-190 530, the complexes of platinum and of vinylated organopolysiloxane which are described in American patents U.S. Pat. No. 3,419,593, U.S. Pat. No. 3,715,334, U.S. Pat. No. 3,377,432 and U.S. Pat. No. 3,814,730.

It is also possible to use the complexes of rhodium which are described in British patents: GB-A-1 421 136 and GB-A-1 419 769.

The platinum catalysts are preferred. In this case, the quantity by weight of catalyst ($I_c$) calculated by weight of platinum metal is generally between 2 and 600 ppm, in general between 5 and 200 ppm based on the total weight of the organosiloxanes ($I_a$) and ($I_b$).

The polyaddition compositions preferred in the context of the present invention are those which comprise:

($I_a$): at least one diorganopolysiloxane oil blocked at each end of its chain with a vinyldiorganosiloxyl unit whose organic radicals linked to the silicon atoms are chosen from methyl, ethyl and phenyl radicals, at least 60 mol % of these radicals being methyl radicals, having a viscosity of 100 to 500 000, preferably of 1 000 to 200 000 mPa·s at 25° C.;

($I_b$): at least one organohydrogenopolysiloxane chosen from the linear or lattice liquid copolymers and homopolymers having per molecule at least 3 hydrogen atoms linked to different silicon atoms and in which the organic radicals linked to the silicon atoms are chosen from methyl and ethyl radicals and at least 60% of these radicals being methyl radicals, the product ($I_b$) being used in a quantity such that the molar ratio of the hydride functions to the vinyl groups is between 1.1 and 4:

($I_c$): a catalytically effective quantity of a platinum catalyst.

More preferably still, up to 50% by weight of the polymer $I_a$ is replaced by a lattice copolymer comprising trimethylsiloxyl, methylvinylsiloxyl and $SiO_{4/2}$ units in which 2.5 to 10 mol % of the silicon atoms comprise a vinyl group and in which the molar ratio of the trimethylsiloxyl groups to the $SiO_{4/2}$ group is between 0.5 and 1.

According to a variant and provided that $C_H$ is less than 1% by weight, the POS composition (I) is a diorganopolysiloxane composition which can be hardened to a silicone elastomer by polycondensation reactions comprising:

($I_{a'}$): at least one diorganopolysiloxane oil carrying at each end of the chain at least two condensable or hydrolysable groups, or a single hydroxyl group, ($I_{b'}$): a silane comprising at least three condensable or hydrolysable groups, and/or a product obtained from the partial hydrolysis of this silane, when (A) is an oil with hydroxyl ends, ($I_{c'}$): a polycondensation catalyst.

The diorganopolysiloxane oils ($I_{a'}$) which can be used in the compositions according to the invention are more particularly those corresponding to the formula (1'):

$$Y_nSi_{3-n}O(SiR_2O)_xSiR_{3-n}Y_n \tag{1'}$$

in which:

R represents identical or different monovalent hydrocarbon radicals and Y represents identical or different hydrolysable or condensable groups, or hydroxyl groups, n is chosen from 1, 2 and 3 with n=1, when Y is a hydroxyl, and x is an integer greater than 1, preferably greater than 10.

The viscosity of the oils of formula (1') is between 50 and $10^6$ mPa·s at 25° C. As examples of R radicals, there may be mentioned alkyl radicals having from 1 to 8 carbon atoms such as methyl, ethyl, propyl, butyl, hexyl and octyl, vinyl radicals, phenyl radicals.

As examples of substituted R radicals, there may be mentioned 3,3,3-trifluoropropyl, chlorophenyl and beta-cyanoethyl radicals.

In the products of formula (1') which are generally used industrially, at least 60% in numerical terms of the R radicals used are methyl radicals, the other radicals being generally phenyl and/or vinyl radicals.

As examples of hydrolysable Y groups, there may be mentioned amino, acylamino, cetiminoxy, iminoxy, enoxy, alkoxy, alkoxyalkyleneoxy, acyloxy and phosphate groups and, for example, among these:

for the Y amino groups: n-butylamino, sec-t-butylamino and cyclohexylamino groups for the N-substituted acylamino groups: the benzoylamino group, for the aminoxy groups: the dimethylaminoxy, diethylaminoxy, dioctylaminoxy and diphenylaminoxy groups, for the iminoxy and citiminoxy groups: those derived from acetophenone oxime, acetone oxime, benzophenone oxime, methylethyl ketoxime, diisopropyl ketoxime and chlorocyclohexanone oxime, for the Y alkoxy groups: the groups having from 1 to 8 carbon atoms such as the methoxy, propoxy, isopropoxy, butoxy, hexyloxy and octyloxy groups, for the Y alkoxyalkyleneoxy groups: the methoxyethyleneoxy group, for the Y acyloxy groups: the groups having from 1 to 8 carbon atoms such as the formyloxy, acetoxy, propionyloxy and 2-ethylhexanoyloxy groups, for the Y phosphate groups: those which are derived from dimethyl phosphate, diethyl phosphate and dibutyl phosphate groups.

As condensable v groups, there may be mentioned hydrogen atoms and halogen atoms, preferably chlorine.

When in the Formula (1') above the Y groups are hydroxyl groups, n is then equal to 1, it is necessary, in order to prepare polyorganosiloxane elastomers from polymers of formula (1') above, to use, in addition to condensation catalysts, crosslinking agents ($I_{b'}$) which are silanes of general formula:

$$R_{4-a}SiY'_a \tag{2'}$$

in which:

R has the meanings given above in formula (1') and Y' represents hydrolysable or condensable groups, which are identical or different, a is equal to 3 or 4.

The examples given for the Y groups are applicable to the Y' groups.

It is desirable to use silanes of formula (2') in the same case where the oil (A) Y is not a hydroxyl group. It is then preferable to use Y groups of the oil ($I_{a'}$) which are identical to the Y' groups of the silane ($I_{b'}$)

The α,ω-dihydroxylated diorganopolysiloxanes of formula (1') are generally oils whose viscosity varies from 500 mPa·s at 25° C. to 500 000 mPa·s at 25° C., preferably 800 to 400 000 mPa·s at 25° C., they are linear polymers essentially consisting of diorganosiloxyl units of formula ($R_2SiO$).

However, the presence of other units, generally at impurities, such as $RSiO_{3/2}$, $RSiO_{1/2}$ and $SiO_{4/2}$, is not excluded in the proportion in particular of at most 1% relative to the number of diorganosiloxyl units.

The organic radicals, linked to the silicon atoms of the parent oils, represented by the symbol R, may be chosen from the alkyl radicals having from 1 to 3 carbon atoms such as the methyl, ethyl and n-propyl radicals, the vinyl radical, the phenyl radical, the 3,3,3-trifluoropropyl radical and the beta-cyanoethyl radical.

Preferably, at least 60% of the whole of the R radicals are methyl radicals, at most 1% are vinyl radicals.

By way of illustration of units represented by the formula $R_2SiO$, there may be mentioned those of formulae:

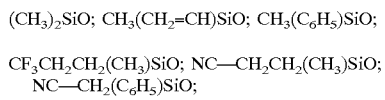

These parent oils are, for the most part, marketed by manufacturers of silicones. Moreover, their manufacturing techniques are well known: they are described for example in French patents FR-A-1 134 005, FR-A-1 198 749, FR-A-1 226 745.

As examples of monomeric silanes $(I_b)$ of formula (2'), there may be mentioned more particularly polyacyloxysilanes, polyalkoxysilanes, polycetiminoxysilanes and polyiminoxysilanes and in particular the following silanes:

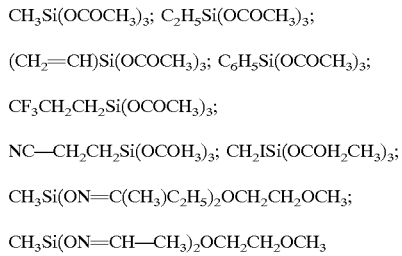

The above $(I_b)$ silanes associated with alpha-omega-dihydroxylated polydiorganosiloxanes of formula (1') may be used in monocomponent compositions which are stable when protected from air.

As examples of monomeric silane of formula (2') which, combined with alpha-omega-dihydroxylated polydiorganosiloxanes of formula (1'), may be advantageously used in bicomponent compositions, there may be mentioned the polyalkoxysilanes and in particular those of formulae:

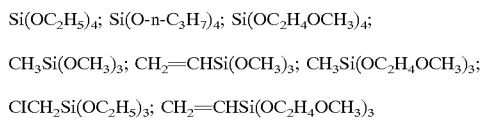

All or some of the monomeric silanes described above may be replaced by polyalkoxysilanes in which each molecule comprises at least two, preferably three Y' atoms, the other valencies of the silicon are satisfied by siloxane bonds SiO and SiR.

As examples of polymeric cross inking agents, ethyl polysilicate may be mentioned.

0.1 to 20 parts by weight of crosslinking agent of formula (2') are generally used per 100 parts by weight of polymer of formula (1').

The polyorganosiloxane compositions which can be hardened to an elastomer of the type described above comprise from 0.001 to 10 parts by weight, preferably from 0.005 to 3 parts by weight of condensation catalyst $(I_c)$ per 100 parts by weight of polysiloxane of formula (1).

The content of condensation catalyst for the monocomponent compositions is generally much smaller than that used in the bicomponent compositions and is generally between 0.001 and 0.05 parts by weight per 100 parts by weight of polysiloxane of formula (2').

The crosslinking agents $(I_b)$ of formula (2'), whether they can be used for the preparation of monocomponent or bicomponent compositions, are products which are accessible on the market for silicones; furthermore, their use in compositions which harden from room temperature upwards is known; it appears in particular in French patents FR-A-1 126 411, FR-A-1 179 969, FR-A-1 189 216, FR-A-1 198 749, FR-A-1 248 826, FR-A-1 314 649, FR-A-1 423 477, FR-A-1 432 799 and FR-A-2 067 636.

According to an advantageous feature of the invention, the POS composition (I), whether it is of the polyaddition type or of the polycondensation type, comprises in addition one or more functional additives $(I_d)$ chosen from the group comprising:

inhibitors of the polyaddition crosslinking reaction, preferably platinum catalyst inhibitors;

reinforcing and/or semireinforcing and/or bulking fillers, plasticizing agents, and mixtures thereof.

The inhibitors are well-known compounds. There may be used in particular organic amines, silazanes, organic oximes, dicarboxylic acid diesters, acetylenic alcohols, acetylenic ketones, vinylmethylcyclopolysiloxanes (see for example U.S. Pat. No. 3,445,420 and U.S. Pat. No. 3,989,667). The inhibitor is used In an amount of form 0.005 to 5 parts by weight, preferably from 0.01 to 3 parts by weight to 100 parts of the constituent $(I_a)$.

The reinforcing or semireinforcing or bulking fillers are preferably chosen from siliceous fillers.

The reinforcing siliceous fillers are preferably chosen from fumed silicas and precipitated silicas. They have a specific surface area, measured according to the BET methods, of at least 50 m²/g, preferably greater than 70 m²/g, a mean primary particle size of less than 0.1 μm (micrometre) and an apparent density of less than 200 g/liter.

These silicas may be incorporated as they are or after having been treated with organosilicon compounds normally used for this use. Among these compounds are methylpolysiloxanes such as hexamethyldisiloxane, octamethyldisiloxane, octamethylcyclotetrasiloxane, methylpolysilazanes such as hexamethyldisilazane, hexamethylcyclotrisilazane, chlorosilanes such as dimethylchlcrcsilane, trimethylchlorosilane, methylvinyldichlorosilane, dimethylvinylchlorosilane, alkoxysilanes such as dimethyldimethoxysilane, dimethylvinylethoxysilane, trimethylmethoxysilane.

During this treatment, the silicas may increase their starting weight up to a level of 20%, preferably 18% approximately.

The semireinforcing or bulking fillers have a particle diameter greater than 0.1 μm and are preferably chosen from ground quartz, calcined clays, diatomaceous earth and aluminium silicates and/or sodium silicates.

The semireinforcing or bulking fillers may also consist of fillers based on alumina and titanium oxide.

From the weight point of view, the fillers may represent from 5 to 100 parts by weight, preferably from 5 to 50 parts by weight per 100 parts of the sum of the POSs $I_a$ or $(I_a)+I_b$ or $(I_b)$ The plasticizing agents capable of constituting additional additives $(_d)$ may be for example liquid paraffin and/or a paraffin.

The POS compositions (I) more especially envisaged in the context of the invention are compositions with two components or with two packagings, also called bicomponent compositions A–B. They are precursors of the elastomers crosslinked at room temperature or by heat in order to accelerate the reaction. This crosslinkage is obtained by mixing components A and B, which are not hardenable separately.

In the case of the preferred polyaddition POS compositions (I), it is desirable that they comprise a crosslinking inhibitor as long as they are in the form of bicomponent compositions in two packagings. Indeed, the inhibition provides a delay which makes it possible to obtain good homogenization of the mixture constituting the EVF 2 or RTV 2//biocide system according to the invention.

To obtain good homogenization of distribution of the active substance, it is indeed desirable for the silicone matrix to have a degree of viscosity of the order of 5 000 to 30 000 mPa·s at 25° C.

Such a viscosity may be obtained by precrosslinking, the latter being blocked at the desired viscosity by addition of an inhibitor. Sufficient time is thus available in order to properly homogenize the active substance inside the silicone matrix.

The crosslinking is then achieved by heating the matrix to a temperature such that the inhibitor no longer has any effect on the catalytic action of platinum.

As regards the biocidal agent (II) used in the system according to the invention, it should be noted that it is preferably chosen from the active chlorine precursor group based on n-chlorinated compounds comprising:

chloramine B (sodium N-chlorobenzenesulphonamide),
chloramine T (sodium N-chloro-p-toluenesulphonamide),
dichloramine T (N,N-dichloro-p-toluenesulphonamide),
N-trichloromethylmercapto-4-cyclohexene-1,2-dicarboxylamide),
halazone (p-n-dichlorosulphonamidebenzoic acid)
N-chlorosuccinide
trichloromelamine

N-chloro derivatives of cyanuric acids, preferably trichloroisocyanuric acid and/or sodium dichloroisocyanuric dihydrate,
N-chlorohydantoins, preferably 1-bromo-3-chloro-5,5'-dimethylhydantoin, or 1,3-dichloro-5, 5'idimethylhydantoin,
and mixtures thereof.

This group of antiseptics essentially corresponds to the N-chloramine family which comprises derivatives of amines in which one or two of the valencies of the trivalent nitrogen are substituted by chlorine. In the presence of water, the N-chloramines produce hypochlorous acid HClO or salts of this acid such as NaClO. HClO is NaClO are active chlorinated derivatives endowed with a high bactericidal capacity, which is exploited in the context of the system according to the invention.

According to an advantageous characteristic of the invention, the system to which it relates is obtained by mixing the POS composition (I) with the biocidal agent in the form of a suspension or a solution, preferably alcoholic.

Advantageously, the biocidal agent (II) is combined with at least one antiseptic auxiliary agent (III) different from the antiseptics which work by releasing chlorine and preferably chosen from the group of surfactant formulations comprising one or more quaternary ammoniums and optionally at least one sequestering activator, preferably selected from metal ion complexing agents.

According to another mode of defining the biocidal agent (II), it may be specified that the latter is advantageously free of inhibitory activity on the crosslinking of the PCS composition (I).

In practice, the system according to the invention may be, for example, such that:

the POS composition (I) comprises:
  ($I_a$): at least one diorganopolysiloxane oil blocked at each end of its chain by a vinyldiorganosiloxyl unit in which the organic radicals linked to the silicon atoms are chosen from methyl, ethyl and phenyl radicals, at least 60 mol % of these radicals being methyl radicals, having a viscosity of 100 to 500 000, preferably of 1 000 to 200 000 mPa·s at 25° C.;
  ($I_b$): at least one organohydrogenopolysiloxane chosen from the linear or lattice liquid copolymers and homopolymers having per molecule at least three hydrogen atoms linked to different silicon atoms and in which the organic radicals linked to the silicon atoms are chosen from methyl and ethyl radicals and at least 60% of these radicals being methyl radicals, the product ($I_b$) being used In a quantity such that the molar ratio of the hydride functions to the vinyl groups is between 1.1 and 4:
  ($I_c$): a catalytically effective quantity of a platinum catalyst.
  ($I_d$): one or more functional additives preferably chosen from the group comprising silicas, aluminas, silicates, vinyl disiloxanes, liquid paraffins, paraffins and mixtures thereof.

the biocidal agent (II) comprises a chloramine, preferably sodium tosylchioramide or one of its chlorinated analogues, the biocidal agent (II) is optionally combined with an antiseptic auxiliary agent (III), preferably benzalkonium chloride, advantageously supplemented with an activator-sequestrant, preferably EDTA.

According to another of its aspects, the invention also relates to a material for taking impressions, in particular dental impressions, comprising a system as defined above.

Advantageously, this material comprises, in addition, adjuvants selected from sweeteners, preferably synthetic sweeteners, and/or from flavourings, and/or from colourings and/or from anti-inflammatory agents, and/or from isotanic products, preferably saccharides, more preferably still hydrogenated saccharides, sorbitol being most especially selected, and mixtures thereof.

By way of example of synthetic sweeteners, there may be mentioned the products marketed under the trade marks ASPARTAM®, ACESULFAM®, and the like.

Mint flavour is among the flavours which can be used.

As an example of an anti-inflammatory adjuvant, allantoin or one of its analogues may be mentioned.

Benzalkonium chloride or one of its analogues is a commercially available surfactant and antiseptic quaternary ammonium.

The biocidal agent (II) used in the context of the invention may be for example a formulation comprising an active chlorine precursor such as a chloramine as well as antiseptic auxiliary agents (III), a sequestering activator and adjuvants. Calbenium having the following composition is an example of these formulations:

| | |
|---|---|
| EDTA (ethylenediamine-tetraacetic acid) or one of its analogues | 100 ± 50 parts by weight |
| Sodium tosylchloramide or one of its analogues | 2 ± 1 part by weight |
| Benzalkonium chloride or one of its analogues | 12 ± 6 parts by weight |
| Aspartame or any synthetic or semisynthetic sweetener | 8 ± 4 parts by weight |
| Mint or any flavouring | 10 ± 5 parts by weight |
| Allantoin or one of its analogues | 6 ± 3 parts by weight |
| Sorbitol or one of its analogues | 132 ± 66 parts by weight | formulation for a dose of 2.5 g necessary for one liter of water.

The present invention also relates to a process for preparing the system or the material as described above. This process is characterized in that it essentially consists in mixing the POS compounds (I), the biocidal agent (II) and optionally the antiseptic auxiliary agent (III) advantageously supplemented with the activator-sequestrant, and optionally the adjuvants as mentioned above.

This mixing is traditionally carried out by appropriate technical means known to persons skilled in the art.

According to an advantageous proposition mentioned above, it is preferable to introduce the biocidal agent II in the form of an alcoholic solution.

The subject of the present invention is also the use of the system or material, as described above, for taking dental impressions, this use being characterized in that it essentially consists in ensuring that the crosslinking of the silicone elastomer is preferably initiated by mixing components A and B, in taking the dental impression and in allowing the crosslinking to continue until the elastomer is sufficiently crosslinked or is sufficiently hard.

The invention will be more clearly understood with the aid of the following examples which describe the preparation of the biocidal silicone elastomer system according to the invention as well as its evaluation in terms of mechanical properties and antiseptic properties.

EXAMPLES

Examples 1 to 3 and Trials 1 to 3

I—In Examples 1 to 3, the crosslinking bicomponents are prepared by polyaddition reactions, leading to the first impression pasty products (so-called type I bicomponents).

1. List of the Raw Materials Used 1.1. - Part A of the bicomponent:

| | |
|---|---|
| POS ($I_a$): | Polydimethylsiloxane oil blocked at each of the ends of the chains by a unit $(CH^3)_2 ViSiO_{0.5}$ of viscosity 100 000 mPa.s and containing about 0.0024 vinyl (Vi) function in 100 g of oil that is about 0.065% by weight of Vi function; |
| POS ($I_{a1}$): | Oil of the same nature as POS ($I_a$) but having a viscosity of 600 mPa.s, containing about 0.014 Vi function in 100 g of oil, that is about 0.38% by weight of Vi function; |
| POS ($1_{a2}$): | retarder of the polyaddition reaction consisting of divinyltetramethyldisiloxane; |
| Functional additives ($I_d$) | |
| Filler 1: | aluminium silicate and sodium silicate, marketed under the name SIPERNAT 44; |
| Filler 2: | hydrate of alumina, marketed under the name ALLUMINA M 15/B; |
| Filler 3: | siliceous material based on diatomaceous earth, marketed under the name DICALITE WHITE FILLER; |
| Ingredient 1: | liquid paraffin; |
| Ingredient 2: | paraffin, marketed under the name PARAFFINE RAFF. LASTRE 52/5; |
| Catalyst ($I_c$): | platinum zero complexed with divinyltetramethyldisiloxane: there is used a solution in divinyltetramethyldisiloxane of a complex of platinum containing about 11% by weight of platinum zero in the form of a ligand with divinyltetramethyldisiloxane; the quantities of this catalyst are expressed as parts by weight of solution used. |

1.2. - Part B of the bicomponent:

| | |
|---|---|
| POS ($I_a$): | cf. part A; |
| POS ($I_{a1}$): | cf. part A; |
| POS ($I_b$): | poly(dimethyl) (methylvinyl)siloxane gum blocked at each of the ends of the chains by a unit $(CH_3)_2ViSiO_{0.5}$ having a weight-average molecular mass of 540 000 g/mol, containing about 0.00185 Vi function in 100 g of gum, that is about 0.05% by weight of Vi function; |
| POS ($1_{b1}$): | poly(dimethyl) (hydrogenomethyl)-siloxane oil blocked at each of the ends of the chains by a unit $(CH_3)_2HiSiO_{0.5}$, having a viscosity of 30 mPa.s and containing about 0.25 H function in 100 g of oil, that is about 0.25% by weight of H; |
| Functional additives ($I_d$) | |
| Filler 1: | cf. part A; |
| Filler 2: | cf. part A; |
| Filler 3: | cf. part A; |
| Ingredient 1: | cf. part A; |
| Ingredient 2: | cf. part A; |
| Bactericide (II): | solution containing 80% by weight of calbenium (80 parts) in ethyl alcohol at 96% (20 parts). |

2. Constitution of Parts A and B of Bicomponents I Tested

| | Part A | Part B |
|---|---|---|
| POS ($I_a$) | 14.45* | 11.4 |
| POS II ($I_{a1}$) | 7.40 | 4.6 |
| POS III ($1_{a2}$) | 0.035 | — |
| POS IV ($I_b$) | — | 4.8 |
| POS V ($I_{b1}$) | — | 2.45 |

-continued

|  | Part A | Part B |  |  |
| --- | --- | --- | --- | --- |
| Functional additives ($I_d$) |  |  |  |  |
| Filler 1 | 40.0 | 31.2 |  |  |
| Filler 2 | 21.0 | 29.6 |  |  |
| Filler 3 | 10.0 | 8.25 |  |  |
| Ingredient 1 | 6.5 | 7.0 |  |  |
| Ingredient 2 | 0.6 | 0.7 |  |  |
| Catalyst ($I_c$) | 0.015 | — |  |  |
| Bactericide (II) | — | Ex. 1 | Ex. 2 | Ex. 3 |
|  |  | 0.25 | 0.75 | 1.25 |

(*: parts by weight)

3. Preparation of the Compositions 3.1—Part A:

(1) The following constituents are introduced, at 23° C., into a planetary mixer: PCS ($I_a$), POS ($I_{a1}$), filler 1 and filler 2; the whole is homogenized by stirring at 20 revolutions/min for 1 hour.

(2) The stirring is then stopped and the filler 3 is then added: another homogenization at revolutions/min for 1 hour.

(3) The stirring is then stopped and the ingredients 1 and 2 are then added: another homogenization at 20 revolutions/min for 1 hour.

(4) The stirring is then stopped and the catalyst and the POS ($I_{a2}$) are then added: another homogenization at 20 revolutions/min for 30 minutes.

(5) Then, without stopping the stirring, the mass is degassed by working at 23° C., under a reduced pressure of 226×10² Pa, for 20 minutes.

3.2—Part B:

The following steps are carried out in the preceding mixer:

(1) Introduction of the POS ($I_a$), POS ($I_{a1}$), POS ($I_b$) filler 1 and filler 2 and homogenization at 23° C., with stirring of 20 rev/min, for 1 hour;

(2) Stoppage of stirring and addition of the filler 3: homogenization for 3 hours at 20 rev/min;

(3) Stoppage of stirring and addition of the ingredients 1 and 2: homogenization for 1 hour at 20 rev/min;

(4) Stoppage of stirring and addition of the bactericide in the desired quantity and of POS ($I_{b1}$): homogenization for 30 minutes at 20 rev/min;

(5) Degassing as indicated above for part A;

3.3. Bicomponents A+B of type I:

The dental RTV composition is obtained by mixing, at room temperature (23° C.), 50 parts by weight of part A and 50 parts by weight of part B. The crosslinking of each bicomponent composition is carried out at room temperature after preparing the mixture.

II—Comparative trials (trials 1 to 3) were carried out using bicomponents of a similar nature, but in which the bactericide consists of benzalkonium chloride (so-called type II bicomponents).

1. List of the Raw Materials Used 1.1. Part A:

POS ($I_a$), POS ($I_{a1}$), PCS ($I_{a2}$) and filler 1: cf. part A, in §I.1.1;

Filler 2: hydrate of alumina, marketed under the name ALLUMINE ALCOA M 10;

Filler 3: siliceous material based on diatomaceous earth, marketed under the name CELITE SUPER FLOS;

Ingredients 1 and 2 and catalyst: cf. part A, in §I-1.1.

1.2. Part B:

POS ($I_a$), POS ($I_{a1}$), POS ($I_b$), POS ($I_{b1}$) and filler 1: cf. part B, in §I-1.2.;

Fillers 2 and 3: cf. part A,; in §II-1.1.;

Ingredients 1 and 2: cf. part B,; in §I-1.2.;

Bactericide (II): solution containing 50% by weight of benzalkonium chloride (50 parts) in ethyl alcohol at 96% (50 parts)

2. Constitution of Parts A and B of the Bicomponents II Tested

|  | Part A | Part B |  |  |
| --- | --- | --- | --- | --- |
| POS ($I_a$) | 14.45* | 11.3 |  |  |
| POS ($I_{a1}$) | 7.40 | 4.0 |  |  |
| POS ($I_{a2}$) | 0.035 | — |  |  |
| POS ($I_b$) | — | 4.8 |  |  |
| POS ($I_{b1}$) | — | 3.1 |  |  |
| Functional additives ($I_d$) |  |  |  |  |
| Filler 1 | 40.0 | 30.8 |  |  |
| Filler 2 | 21.0 | 28.8 |  |  |
| Filler 3 | 10.0 | 8.9 |  |  |
| Ingredient 1 | 6.5 | 7.0 |  |  |
| Ingredient 2 | 0.6 | 0.7 |  |  |
| Catalyst ($I_c$) | 0.015 | — |  |  |
| Bactericide (II) | — | Trial 1 | Trial 2 | Trial 3 |
|  |  | 0.5 | 1.0 | 2.0 |

(*: parts by weight)

3. Preparation of the Compositions 3.1—Part A:

The procedure is carried out as above in §I-3.1.

3.2—Part B:

The procedure is carried out as indicated above in §I-3.2., but with the following slight modifications:

| step (1) to (5): | stirring at 50 revolutions/min; |
| --- | --- |
| step (3): | addition of ingredients 1 and 2 and of the bactericide; |
| step (4): | addition of the sole POS V and homogenization for 1 hour. |

3.3. Bicomponents A+B of type II:

The crosslinking of the bicomponent is carried out, as indicated above in §I-3.3., at room temperature after mixing the 2 parts A and B in a 50/50 ratio by weight.

III—Results

They are assembled in Table 1 below. This table indicates the contents of bactericidal agent which were introduced according to the technique described above, as well as the working time and the setting time for the products obtained. The working time corresponds to the time during which the mixture of the 2 parts A and B retains a fluid behaviour; beyond, the material acquires the characteristics of an elastomer. The setting time corresponds to the time necessary for the dental impression to become capable of being handled.

TABLE I

| Bicomponent type | Ex. 1 I | Ex. 2 I | Ex. 3 I | Trial 1 II | Trial 2 II | Trial 3 II |
|---|---|---|---|---|---|---|
| Bactericide | | | | | | |
| nature: | calbenium | calbenium | calbenium | benzalkonium chloride | benzalkonium chloride | benzalkonium chloride |
| % by weight in A + b | 0.1 | 0.3 | 0.5 | 0.125 | 0.25 | 0.5 |
| Initial properties measured after preparation of parts A and B and mixtures thereof: | | | | | | |
| working time: | 1 min 50 s | 1 min 50 s | 2 min | 2 min | 2 min 15 s | 2 min 30 s |
| setting time | 2 min 20 s | 2 min 30 s | 2 min 50 s | 5 min | 6 min | 6 min 30 s |
| Properties measured after storing parts A and B separated $x$ days at 23° C.: | $x = 180$ | $x = 180$ | $x = 180$ | | | $x = 30$ |
| working time: | 2 min | 2 min 50 s | 2 min 10 s | | | — |
| setting time: | 2 min 30 s | 2 min 50 s | 3 min | | | >10 min |

Examples 4 to 6 and Trials 4 to 6

I—In Examples 4 to 6, bicomponents crosslinking by polyaddition reactions are prepared, leading to second impression fluid products (so-called type III bicomponents).

1. List of the Raw Materials Used

1.1. Part A:

| | |
|---|---|
| POS ($I_a$) and ($I_{a1}$): | cf. part A, Examples 1–3, § I-1.1.; |
| Functional additives ($I_d$) | |
| Filler 4: | fumed silica, marketed under the name AEROSIL 200, treated with hexamethyldisilazane; |
| Filler 5: | ground quartz having a mean particle diameter of 10 μm, marketed under the name SICRON SA 600; |
| Filler 6: | $TiO_2$; |
| Ingredient 3: | polyoxyethylated and propylated $C_8$–$C_{10}$ fatty alcohol, marketed under the name SOPROFOR BO 327; |
| Catalyst ($I_c$): | cf. part A, Examples 1–3, § I-1.1. |

1.2. - Part B:

| | |
|---|---|
| POS ($I_a$) and ($I_{a1}$): | cf. part A, immediately above; |
| POS ($I_{b1}$): | cf. part B, Example 1–3, § I-1.2.; |
| Functional additives ($I_d$) | |
| Fillers 4, 5 and 6: | cf. part A, immediately above; |
| Ingredient 3: | cf. part A, immediately above; |
| Bactericide: | solution containing 80% by weight of calbenium (80 parts) in ethyl alcohol at 96% (20 parts). |

2. Constitution of Parts A and B of the Bicomponents III tested

| | Part A | Part B | | |
|---|---|---|---|---|
| POS ($I_a$) | 2.0* | 6.0 | | |
| POS ($I_{a1}$) | 52.0 | 42.3 | | |
| POS ($I_{b1}$) | — | 8.0 | | |
| Functional additives ($I_d$) | | | | |
| Filler 4 | 12.0 | 12.0 | | |
| Filler 5 | 34.5 | 35.0 | | |
| Filler 6 | 0.6 | 0.5 | | |
| Ingredient 3 | 0.3 | 0.3 | | |
| Catalyst ($I_c$) | 0.01 | — | | |
| Bactericide (II) | — | Ex. 4 0.25 | Ex. 5 0.75 | Ex. 6 1.25 |

(*: parts by weight)

3. Preparation of the Compositions

3.1—Part A:

(1) In a first instance, a basic mixture (abbreviated BM) is prepared by mixing at room temperature (23° C.) 24 parts by weight of filler 4 and 56 parts by weight of POS (II).

(2) For the preparation of part A, 40 parts of BM are mixed in a turbine dispersing device with POS I, the remainder of POS (II) (24 parts), the fillers 5 and 6 and the ingredient 3: the procedure is carried out at 23° C., with stirring at 450 rev/min, for 2 hours.

(3) The stirring is then stopped and then it is checked that the temperature of the mass is ≦70° C. before adding the catalyst: homogenization for 10 minutes at 450 rev/min, and then degassing of the mass, the procedure being carried out under a reduced pressure of 266×10² Pa for 10 minutes.

3.2—Part B:

(1) 40 parts of the remaining BM are mixed with the POS ($I_a$), the remainder of POS ($I_a$), the remainder of POS ($I_{a1}$) (14.3 parts), the fillers 5 and 6 and the ingredient 3: next, homogenization for 1 hour at 450 rev/min.

(2) he stirring is then stopped and POS ($I_{b1}$) is then added: the homogenization is then resumed for 10 minutes at 450 rev/min.

(3) Another stopping of the stirring and, after having checked that the temperature of the mass is ≦70° C., the bactericide is added: next, homogenization for 10 minutes at 450 rev/min; then degassing as indicated above, at the end of part A.

3.3. Bicomponents A+B of type III:

The crosslinking of the bicomponents is carried out, here again, at room temperature (23° C.) after mixing the 2 parts A and B in a 50/50 ratio by weight. II—Comparative trials (trials 4 to 6) were carried out using bicomponents of a similar nature, but in which the bactericide consists of benzalkonium chloride (so-called type IV bicomponents).

1. List of the Raw Materials Used

1.1. Part A:

| | |
|---|---|
| POS ($I_a$) and ($I_{a1}$): | cf. part A, Examples 4–6, § I-1.1.; |
| POS ($I_{a2}$): | cf. part A, Examples 1–3, § I-1.1.; |
| Functional additives ($I_d$) | |
| Fillers 4, 5 and 6: | cf. part A, Examples 4–6, § I-1.1.; |
| Filler 7: | fumed silica, marketed under the name AEROSIL 200, treated with octamethylcyclotetrasiloxane; |
| Ingredient 3 and catalyst ($I_c$): | cf. part A, Examples 4–6, § I-1.1. |

1.2. Part B:

| | |
|---|---|
| POS ($I_a$) and ($I_{b2}$) + fillers 4 and 5 + ingredient 3: | cf. part B, Examples 4–6, § I-1.2.; |
| Bactericide: | solution containing 50% by weight of benzalkonium chloride (50 parts) in ethyl alcohol at 96% (50 parts) |

2. Constitution of Parts A and B of the Bicomponents IV Tested

| | Part A | Part B |
|---|---|---|
| POS ($I_a$) | 2.0 | — |
| POS ($I_{a1}$) | 49.46 | 40.7 |
| POS ($I_{a2}$) | 0.03 | — |
| POS ($I_{b2}$) | — | 11.0 |

-continued

| | Part A | Part B | | |
|---|---|---|---|---|
| Functional additives ($I_d$) | | | | |
| Filler 4 | 12.4 | 14.6 | | |
| Filler 5 | 34.5 | 34.0 | | |
| Filler 6 | 0.5 | — | | |
| Filler 7 | 1.0 | — | | |
| Ingredient 3 | 0.1 | 0.3 | | |
| Catalyst ($I_c$) | 0.01 | — | | |
| Bactericide (II) | — | Trial 5 | Trial 6 | Trial 7 |
| | | 0.5 | 1.0 | 2.0 |

(*: parts by weight)

3 Preparation of the Compositions 3.2—Part A:

The procedure is carried out as indicated above in §I-3.1. of Examples 4 to 6, but with the following modifications:

step (1): the BM is prepared by mixing 27 parts by weight of filler 4 and 63 parts by weight of POS ($I_{a1}$);

step (2): 41.3 parts of the BM are mixed with the POS ($I_a$) the remainder of POS ($I_{a1}$) (20.55 parts), the fillers 5, 6 and 7 and the ingredient 3;

step (3): the catalyst and the PCS ($I_{a2}$) are added.

3.2—Part B:

The procedure is carried out as indicated above in §I-3.2. of Examples 4 to 6, but with the following modifications:

step (1): 48.7 parts of the rest of the BM are mixed with the remainder of POS ($I_{a1}$) (6.61 parts);

step (2): there are added thereto the filler 5 in place of POS ($I_{b1}$) and the mixture is homogenized for 2 hours;

step (3): there are added, this time, apart from the bactericide, the POS ($I_{b1}$) and the ingredient 3, and the mixture 5s homogenized for 1 hour 30 minutes.

3.2. Bicomponents A+B of type IV:

The crosslinking of the bicomponents is carried out, here again, at room temperature (23° C.) after mixing the two parts A and B in a 50/50 ratio by weight.

III—Results

They are assembled in the following Table 2.

TABLE 2

| Bicomponent type | Ex. 4 III | Ex. 5 III | Ex. 6 III | Trial 4 IV | Trial 5 IV | Trial 6 IV |
|---|---|---|---|---|---|---|
| Bactericide | | | | | | |
| nature: | calbenium | calbenium | calbenium | benzalkonium chloride | benzalkonium chloride | benzalkonium chloride |
| % by weight in A + B | 0.1 | 0.3 | 0.5 | 0.125 | 0.25 | 0.5 |
| Initial properties measured after preparation of parts A and B and mixtures thereof: | | | | | | |
| working time: | 2 min 30 s | 2 min 40 s | 2 min 50 s | 2 min | 3 min | 4 min |
| setting time | 5 min 10 s | 6 min | 8 min | 5 min | 8 min | >15 min |
| Properties measured after storing parts A and B separated $x$ days at 23° C.: | $x$ = 180 | $x$ = 180 | $x$ = 180 | | | $x$ = 30 |
| working time: | 2 min 30 s | 2 min 50 s | 2 min 55 s | | | — |
| setting time: | 5 min 20 s | 6 min 15 s | 8 min 20 s | | | >30 min |

Example 7—Bactericidal Activity

The bactericidal activities of the systems according to Examples 1 to 6 and according to trials 1 to 6 were evaluated in the following manner.

Films whose thickness is 2 mm and whose side is 2.5 cm are prepared by crosslinking, at room temperature, an appropriate mixture of parts A and B of the systems tested.

The silicone squares are soaked in a bacterial suspension of *Staphylococcus aureus* having a titre of 105 CFU/ml, so that the microorganisms are in contact both with the edge and the surface of the squares.

After a contact time of 30 min, the films are removed and kept under relative humidity conditions (STP 50), this being up to the time of placing in culture, that is after 6 h, 24 h, 3 days and one week, and at laboratory temperature.

The culture will be carried out by inclusion in Trypticase soybean medium and agar at 37±1° C. for 24 to 48 hours Before the incubation, the agars are inoculated with a *Staphylococcus aureus* culture (8×10$^4$ CFU), this strain having been chosen as microorganism representative of the buccal medium.

Controls free of silicone elastomer biocides of the same type as systems according to Examples 1 to 6 are used.

Results

|  | Control | Biocidal silicone systems Ex. 1 to 6 |
|---|---|---|
| Culture after 6 h of contact | Numerous colonies (about 300 CFU/dish) | A few colonies survive (about 300 CFU/dish) |
| Culture after 24 h of contact | Growth on the silicones (about 100 CFU/dish) | All negative |
| Culture after 3 days of contact | Growth on the silicones (about 36 CFU/dish) | All negative |
| Culture after 7 days of contact |  | All negative |

What is claimed is:

1. A silicone elastomer system which comprises:
   I. at least one polyorganosiloxane (POS) composition comprising a polyaddition silicone composition capable of hardening to an elastomer by hydrosilation, said polyaddition silicone composition comprising:
      ($I_a$) at least one diorganopolysiloxane oil having, per molecule, at least two alkenyl groups linked to the silicon;
      ($I_b$) at least one diorganopolysiloxane oil having, per molecule, at least three hydrogen atoms linked to the silicon;
      ($I_c$) a catalytically effective quantity of a catalyst which is a compound of a metal of the platinum group; and
   II. at least one biocidal agent selected from the group consisting of:
      chloramine B (sodium N-chlorobenzene-sulphonamide),
      chloramine T (sodium N-chloro-p-toluene-sulphonamide),
      dichldramine T (N,N-dichloro-p-toluene-sulphonamide),
      N-trichloromethylmercapto-4-cyclohexene-1,2-dicarboxylamide,
      halazone (p-n-dichlorosulphonamidebenzoic acid),
      N-chlorosuccinide,
      trichloromelamine,
      N-chlorohydantoins,
      1,3-dichloro-5,5'dimethylhydantoin,
      and mixtures thereof.

2. The system according to claim 1, wherein the concentration $C_{II}$ of biocidal agent, expressed in % by weight relative to the total mass (I+II), is:
   $C_{II}<1$.

3. The system according to claim 2, wherein the concentration of biocidal agent is: $C_{II} \leq 0.8$.

4. The system according to claim 4, wherein the concentration of biocidal agent is: $C_{II} \leq 0.5$.

5. The system according to claim 1, wherein the POS composition (I) comprises in addition, one or more functional additives ($I_d$) selected from the group consisting of:
   inhibitors of the polyaddition crosslinking reaction;
   reinforcing and/or semireinforcing and/or bulking fillers,
   plasticizing agents, and
   mixtures thereof.

6. The system according to claim 1, wherein the POS composition (I) is a bicomponent composition A–B, a precursor of the elastomer crosslinked at room temperature or by heat, by mixing components A and B, which are not hardenable separately.

7. The system according to claim which is obtained by mixing the POS composition (I) with the biocidal agent (II) in the form of a suspension or a solution.

8. The system according to claim 1, wherein the biocidal agent (II) is combined with at least one antiseptic auxiliary agent (III) different from said biocidal agent (II) and optionally at least one sequestering activator.

9. The system according to claim 1, wherein the biocidal agent (II) is tree of inhibitory activity on the crosslinking of the POS composition (I).

10. The system according to claim 1, wherein:
    the POS composition (I) comprises:
    ($I_a$): at least one diorganopolysiloxane oil blocked at each end of its chain by a vinyldiorganosiloxyl unit in which the organic radicals linked to the silicon atoms are chosen from methyl, ethyl and phenyl radicals, at least 60 mol % of these radicals being methyl radicals, having a viscosity of 100 to 500 000 mPa·s at 25° C.;
    ($I_b$): at least one organohydrogenopolysiloxane selected from the group consisting of linear or lattice liquid copolymers and homopolymers having per molecule at least three hydrogen atoms linked to different silicon atoms and in which the organic radicals linked to the silicon atoms are selected from methyl or ethyl radicals and at least 60% mole of these radicals being methyl radicals, the product ($I_b$) being used in a quantity such that the molar ratio of the hydride functions to the vinyl groups is between 1.1 and 4;
    ($I_c$) a catalytically effective quantity of a platinum catalyst;
    ($I_d$) one or more functional additives comprising silicas, aluminas, silicates, vinyl disiloxanes, liquid paraffins, paraffins or mixtures thereof;
    the biocidal agent (II) comprises a chloramine; and
    the biocidal agent (II) is optionally combined with an antiseptic auxiliary agent (III), optionally supplemented with an activator-sequestrant.

11. The system according to claim 10, wherein the biocidal agent (II) comprises sodium tosylchloramide, the antiseptic auxiliary agent (III) comprises a benzalkonium chloride and the activator-sequestrant comprises EDTA.

12. A material for taking an impression, which comprises a system according to, claim 1.

13. The material according to claim 12, which additionally comprises at least one adjuvant selected from the group consisting of sweeteners, flavourings, colourings, anti-inflammatory agents, isotonic products, and mixtures thereof.

14. A process for preparing the system according to claim 1, comprising mixing the POS compounds (I), the biocidal agent (II) and any optional ingredients.

15. A process for preparing a system according to claim 1 for taking a dental impression, comprising initiating crosslinking of the silicone elastomer, taking the dental impression and allowing the crosslinking to continue until the elastomer is hardened.

16. The system according to claim 1, wherein the N-chlorohydantoins comprise 1-bromo-3-chloro-5,5'-dimethyl hydantoin or 1,3-dichloro-5,5'-dimethylhydantoin.

* * * * *